United States Patent
Wildes et al.

(10) Patent No.: US 10,347,818 B2
(45) Date of Patent: Jul. 9, 2019

(54) METHOD FOR MANUFACTURING ULTRASOUND TRANSDUCERS

(71) Applicant: General Electric Company, Schenectady, NY (US)

(72) Inventors: Douglas Glenn Wildes, Ballston Lake, NY (US); Lowell Scott Smith, Schenectady, NY (US); Kwok Pong Chan, Elmhurst, NY (US); Vadim Bromberg, Schenectady, NY (US)

(73) Assignee: General Electric Company, Schenectady, NY (US)

( * ) Notice: Subject to any disclaimer, the term of this patent is extended or adjusted under 35 U.S.C. 154(b) by 416 days.

(21) Appl. No.: 15/087,369

(22) Filed: Mar. 31, 2016

(65) Prior Publication Data
US 2017/0288638 A1    Oct. 5, 2017

(51) Int. Cl.
*H01L 41/33* (2013.01)
*H01L 41/27* (2013.01)
(Continued)

(52) U.S. Cl.
CPC .......... *H01L 41/33* (2013.01); *B06B 1/0622* (2013.01); *H01L 41/047* (2013.01); *H01L 41/09* (2013.01); *H01L 41/113* (2013.01); *H01L 41/27* (2013.01); *H01L 41/277* (2013.01); *H01L 41/29* (2013.01); *H03H 3/02* (2013.01); *H03H 9/205* (2013.01); *A61B 8/4281* (2013.01); *A61B 8/4444* (2013.01); *A61B 8/4483* (2013.01);
(Continued)

(58) Field of Classification Search
CPC .. H03H 3/02; H03H 9/205; H03H 2003/0478; B06B 1/0622; A61B 8/4281; A61B 8/4483; A61B 8/4444; H01L 41/047; H01L 41/09; H01L 41/113; H01L 41/27; H01L 41/277; H01L 41/29; H01L 41/33; Y10T 29/42; Y10T 29/49005; Y10T 29/49798
See application file for complete search history.

(56) References Cited

U.S. PATENT DOCUMENTS 3,981,184 A    9/1976  Matay
4,385,255 A *  5/1983  Yamaguchi ........... B06B 1/0622
                                                    29/25.35
(Continued)

FOREIGN PATENT DOCUMENTS

JP    2012182758 A  *  9/2012

OTHER PUBLICATIONS

Vogel, "Transducers with Screen Printed Matching Layers", IEEE 1985 Ultrasonics Symposium, pp. 704-710, Oct. 16-18, 1985.
(Continued)

*Primary Examiner* — A. Dexter Tugbang (57) ABSTRACT

A manufacturing a process is provided for the bulk manufacture of transducer arrays, including arrays having at least one 3D printed (or otherwise additive manufactured) acoustic matching layers. In certain implementations, the manufactured transducers include a composite-piezoelectric transducer on a de-matching layer. In one implementation, by producing multiple arrays at once on a common carrier, and by using direct-deposit additive processes for the matching layers, the described processes greatly reduce the number of parts and the number of manual operations.

16 Claims, 6 Drawing Sheets

(51) Int. Cl.
    *B06B 1/06*     (2006.01)
    *H03H 3/02*     (2006.01)
    *H01L 41/047*     (2006.01)
    *H01L 41/09*     (2006.01)
    *H01L 41/113*     (2006.01)
    *H01L 41/277*     (2013.01)
    *H01L 41/29*     (2013.01)
    *H03H 9/205*     (2006.01)
    *A61B 8/00*     (2006.01)
    *H03H 3/04*     (2006.01)

(52) U.S. Cl.
    CPC ...... *H03H 2003/0478* (2013.01); *Y10T 29/42* (2015.01); *Y10T 29/49005* (2015.01); *Y10T 29/49798* (2015.01)

(56) References Cited

U.S. PATENT DOCUMENTS

| | | | |
|---|---|---|---|
| 4,385,634 A | | 5/1983 | Bowen |
| 4,458,689 A | | 7/1984 | Sorenson et al. |
| 4,506,354 A | | 3/1985 | Hansen |
| 4,593,567 A | | 6/1986 | Isselstein et al. |
| 4,747,192 A | | 5/1988 | Rokurota |
| 4,773,140 A | | 9/1988 | McAusland |
| 4,825,115 A | | 4/1989 | Kawabe et al. |
| 4,890,580 A | | 1/1990 | Owen et al. |
| 4,979,994 A | | 12/1990 | Dussault et al. |
| 5,027,822 A | * | 7/1991 | Gelly .................. B06B 1/0622 29/25.35 |
| 5,149,986 A | | 9/1992 | Jalbert |
| 5,201,453 A | | 4/1993 | Amador |
| 5,351,691 A | | 10/1994 | Brommersma |
| 5,360,005 A | | 11/1994 | Wilk |
| 5,381,795 A | | 1/1995 | Nordgren |
| 5,482,047 A | | 1/1996 | Nordgren |
| 5,617,864 A | | 4/1997 | Stouffer et al. |
| 5,697,248 A | | 12/1997 | Brown |
| 5,844,349 A | | 12/1998 | Oakley et al. |
| 5,865,650 A | | 2/1999 | Marian, Jr. et al. |
| 5,951,304 A | | 9/1999 | Wildes et al. |
| 6,016,821 A | | 1/2000 | Puskas |
| 6,110,314 A | | 8/2000 | Nix et al. |
| 6,308,389 B1 | | 10/2001 | Tezuka |
| 6,371,918 B1 | | 4/2002 | Bunce |
| 6,640,634 B2 | | 11/2003 | Hashimoto |
| 6,659,954 B2 | | 12/2003 | Robinson |
| 6,822,376 B2 | | 11/2004 | Baumgartner |
| 7,053,530 B2 | | 5/2006 | Baumgartner et al. |
| 7,275,298 B2 | | 10/2007 | Schindel |
| 7,573,181 B2 | | 8/2009 | Rhim et al. |
| 7,621,028 B2 | | 11/2009 | Gelly et al. |
| 7,764,006 B2 | * | 7/2010 | Tsukamura ............ Y10T 29/42 310/328 |
| 7,908,721 B2 | | 3/2011 | Zipparo et al. |
| 8,084,923 B2 | | 12/2011 | Guo |
| 8,207,652 B2 | | 6/2012 | Baumgartner et al. |
| 8,208,346 B2 | | 6/2012 | Crunkilton |
| 8,674,587 B2 | | 3/2014 | Togasaki et al. |
| 8,737,170 B2 | | 5/2014 | Kasper |
| 8,742,646 B2 | | 6/2014 | Wodnicki et al. |
| 8,914,245 B2 | | 12/2014 | Hopkins |
| 8,974,393 B2 | | 3/2015 | Cho et al. |
| 8,996,319 B2 | | 3/2015 | Cokonaj |
| 2008/0125658 A1 | | 5/2008 | Lee et al. |
| 2009/0069689 A1 | | 3/2009 | Isono |
| 2014/0257109 A1 | | 9/2014 | Nishikubo |

OTHER PUBLICATIONS

Ramadas et al., "Tapered Transmission Line Technique Based Graded Matching Layers for Thickness Mode Piezoelectric Transducers," Ultrasonics Symposium (IUS), 2009 IEEE International, pp. 1695-1698, Sep. 20-23, 2009.

* cited by examiner

METHOD FOR MANUFACTURING ULTRASOUND TRANSDUCERS

BACKGROUND

The subject matter disclosed herein relates to the bulk fabrication of piezoelectric ultrasound transducer arrays.

At present, ultrasound transducers are produced via expensive and labor-intensive processes. These processes may include steps for grinding, lapping, and dicing different materials to precise thicknesses and dimensions, cleaning and surface treating the individual parts, aligning and gluing them together, then dicing to create an array. Further, each transducer array is manufactured individually, leading to low volume manufacturing. The cumulative effect of so many manual steps limits product repeatability, leading to lower yield, and less product uniformity.

In order for ultrasound imaging to expand from premium and mid-tier diagnostic imaging to primary care and rural applications, including into developing countries, a low-cost process amenable to automation and high volume production is needed.

BRIEF DESCRIPTION

In one implementation, a method for fabricating ultrasound transducers is provided. In accordance with this method, a piezoelectric transducer layer is provided at an initial thickness and a signal electrode is formed on one surface of the piezoelectric transducer layer to form a signal surface of the piezoelectric transducer layer. A de-matching layer is positioned against the signal electrode opposite the piezoelectric transducer layer and the de-matching layer and the piezoelectric transducer layer are positioned on a carrier. A plurality of isolation cuts is made through both the piezoelectric transducer layer and the de-matching layer. The isolation cuts isolate the transducer elements from a ground path. A plurality of composite cuts is made through the piezoelectric transducer layer but not the de-matching layer and the isolation cuts and the composite cuts are filled with a first material. A plurality of element cuts is made through both the piezoelectric transducer layer and the de-matching layer. The element cuts run perpendicular to the isolation cuts and define transducer elements within each transducer array. The element cuts are filled with the first material or with a second material. The piezoelectric transducer layer is ground to a specified thickness and a plurality of initial dicing cuts is made through both the piezoelectric transducer layer and the de-matching layer. The initial dicing cuts define two or more transducer arrays. A wrap-around ground electrode is formed over the diced piezoelectric transducer layer and the de-matching layer. The wrap-around ground electrode connects the signal surface and a ground surface of the piezoelectric transducer layer without blocking an acoustic path of respective transducer arrays. One or more acoustic matching layers are formed over the piezoelectric transducer layer opposite the de-matching layer. At least one acoustic matching layer is formed using additive manufacturing processes. The one or more acoustic matching layers includes a plurality of additional cuts or voids through the one or more acoustic matching layers and corresponding to the initial dicing cuts. A stack assembly including at least the one or more acoustic matching layers, the piezoelectric transducer layer, and the de-matching layer is released from the carrier, wherein a plurality of transducer arrays corresponding to the stack assembly regions defined by the dicing cuts is released.

In another implementation, a method for fabricating ultrasound transducers is provided. In accordance with this method, a piezoelectric transducer layer is provided at an initial thickness. An electrode is formed on one surface of the piezoelectric transducer layer to form a signal surface of the piezoelectric transducer layer. A de-matching layer is positioned against the signal surface opposite the piezoelectric transducer layer and the de-matching layer and the piezoelectric transducer layer are positioned on a carrier. A plurality of isolation cuts is made through both the piezoelectric transducer layer and the de-matching layer. The isolation cuts isolate the transducer elements from a ground path. The isolation cuts are filled with a first material. A plurality of element cuts is made through both the piezoelectric transducer layer and the de-matching layer. The element cuts run perpendicular to the isolation cuts and define transducer elements within each transducer array. The element cuts are filled with the first material or with a second material. The piezoelectric transducer layer is ground to a specified thickness and a plurality of initial dicing cuts is made through both the piezoelectric transducer layer and the de-matching layer. The initial dicing cuts define two or more transducer arrays. A wrap-around ground electrode is formed over the diced piezoelectric transducer layer and the de-matching layer. The wrap-around ground electrode connects the signal surface and a ground surface of the piezoelectric transducer layer without blocking an acoustic path of respective transducer arrays. One or more acoustic matching layers are formed over the piezoelectric transducer layer opposite the de-matching layer. At least one acoustic matching layer is formed using additive manufacturing processes. The one or more acoustic matching layers includes a plurality of additional cuts or voids through the one or more acoustic matching layers and corresponding to the initial dicing cuts. A stack assembly including at least the one or more acoustic matching layers, the piezoelectric transducer layer, and the de-matching layer is released from the carrier, wherein a plurality of transducer arrays corresponding to the stack assembly regions defined by the dicing cuts is released.

In a further implementation, an ultrasound transducer array is provided. In accordance with certain aspect, the ultrasound transducer array includes a piezoelectric transducer layer including signal electrode on a signal surface of the piezoelectric transducer layer; a de-matching layer positioned on the signal surface side of the piezoelectric transducer; a plurality of isolation cuts formed through both piezoelectric transducer layer and the de-matching layer and filled with a first material, wherein the isolation cuts isolate the transducer elements from a ground path; a plurality of element cuts formed through both the piezoelectric transducer layer and the de-matching layer and running perpendicular to the isolation cuts, wherein the plurality of element cuts are filled with the first material or a second material and define transducer elements within each transducer array; a wrap-around ground electrode formed over the piezoelectric transducer layer and the de-matching layer, wherein the wrap-around ground electrode connects the signal surface and a ground surface of the piezoelectric transducer layer without blocking an acoustic path of respective transducer arrays; one or more acoustic matching layers formed over the piezoelectric transducer layer opposite the de-matching layer, wherein at least one acoustic matching layer is formed using additive manufacturing processes.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

One or more specific implementations will be described below. In an effort to provide a concise description of these implementations, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present subject matter, the articles "a," "an," "the," and "said" are intended to mean that there are one or more of the elements. The terms "comprising," "including," and "having" are intended to be inclusive and mean that there may be additional elements other than the listed elements.

A high-volume, automated process for manufacturing ultrasound transducers is described herein. In accordance with this process, the manufactured ultrasound transducer arrays include a high-impedance de-matching layer, a piezoelectric ceramic layer, and one or more acoustic matching layers. These layers as described herein, are created on a carrier substrate, then removed and bonded to electrical interconnect and backing structures, such as using automated processes. In one implementation, the acoustic matching layers are created in-place using additive manufacturing processes. The piezoelectric ceramic layer may be made into a 1-3 or 2-2 composite during the transducer fabrication process.

Figure 1:
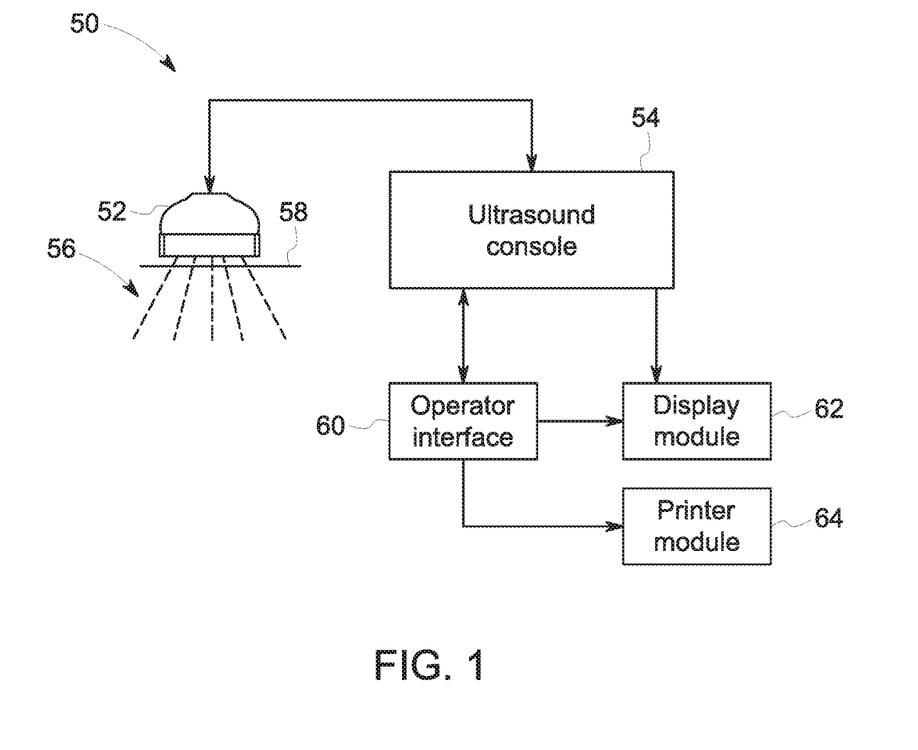
FIG. 1 depicts an ultrasound system having a probe using a piezoelectric transducer array, in accordance with aspects of the present disclosure.

With the preceding in mind, FIG. 1 provides a brief overview of an ultrasound imaging system in which the transducers described herein may be used. In the depicted example, the ultrasound system 50 includes an ultrasound probe 52 and an ultrasound console 54 suitable for generating and receiving ultrasound signals via the probe 52. In accordance with present implementations, the probe 52 includes a transducer array produced in accordance with the techniques discussed herein. Such a transducer array may include a de-matching layer in conjunction with a piezoelectric transducer layer and one or more acoustic matching layers. The piezoelectric transducer layer may be formed as a 1-3 or 2-2 composite during fabrication.

In certain embodiments, the ultrasound console 54 may include beam-formers and image reconstruction and processing circuitry used to direct the ultrasonic energy 56 into the tissue 58 of a patient and to reconstruct the return signals measured at the probe 52. For example, the ultrasound console 54 may control the strength, beam focus or forming, duration, phase, and frequency of the ultrasound signals transmitted by the ultrasound probe 52, and may decode the information contained in the plurality of reflected ultrasound signals from the tissue to a plurality of discernible electrical and electronic signals. The return signals may be processed at the console 54 to generate images of the anatomic region of interest underlying the probe 52.

The ultrasound system 50 may also include an operator interface 60 allowing a user to interact with and control the console 54. The operator interface 60 may include a keyboard, a mouse, and other user interaction devices. The operator interface 60 can be used to customize a plurality of settings for an ultrasound imaging procedure, to effect system level configuration changes, and to allow operator activation and operation of the ultrasound system 50.

In the depicted example, the operator interface 60 is connected to the ultrasound console 54, a display module 62, and a printer module 64, some or all of which may be provided as an ultrasound workstation. The display module 62 receives image information from the ultrasound console 54 and presents the image of the objects underlying the ultrasound probe 52. The printer module 64 is used to produce a hard copy of the ultrasound image in either gray-scale or color. In general, the reflected ultrasound signals and corresponding images convey information about thickness, size, and location of various tissues, organs, tumors, and anatomical structures in relation to transmitted ultrasound signals.

Figure 2:
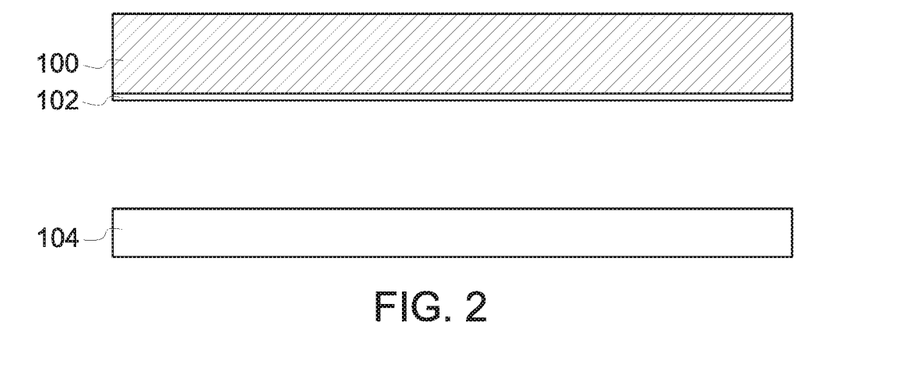
FIG. 2 depicts an initial fabrication step of providing a piezoelectric transducer layer and a de-matching layer, in accordance with aspects of the disclosure.

With these features in mind, and turning to FIG. 2, a walk-through of an example of a manufacturing process is provided. As shown in FIG. 2, a piezoelectric transducer layer 100 (such as a layer of lead zirconate titanate (PZT)) is initially provided. In one implementation, the piezoelectric transducer layer 100 is a piezoelectric ceramic layer. The piezoelectric transducer layer 100 may have a thickness that is greater initially than it will be in its finished form. In one implementation, the piezoelectric transducer layer 100 undergoes a grinding and/or lapping process on one surface (i.e., a bottom surface). An electrode 102 is then formed using one or more standard metallization techniques (such as sputtering, plating) and/or additive manufacturing/3D printing processes (such as controlled dispensing, jetting, and so forth) and curing of a highly conductive ink (e.g., nanoparticle- or organometallic-based silver, copper, or gold) on this bottom surface, which constitutes the signal side of the piezoelectric transducer layer 100.

A de-matching layer 104, such as a high-impedance de-matching layer, is also provided initially. As with the piezoelectric transducer layer 100, the de-matching layer 104 may also undergo a grinding and/or lapping process to achieve the specified final thickness and/or surface finish. The de-matching layer 104 may be formed from tungsten carbide (WC) or other suitable materials and functions as a node-material that acts to change the effective resonant frequency generated by the piezoelectric material. The presence of the de-matching layer 104 and its effect on the resonant frequency of the piezoelectric transducer layer 100 allows a thinner piezoelectric transducer layer 100 to be employed while still obtaining the desired range of frequencies.

As discussed herein, the de-matching layer 104 is a conductive structure, which eliminates the need for a continuous wrap-around ground electrode on the piezoelectric transducer being fabricated. By way of example, and as discussed in greater detail below, in one implementation the elevation edges of the array are diced and metalized after the piezoelectric transducer layer 100 and de-matching layer 104 are laminated. The resulting electrode is continuous from the piezoelectric transducer layer 100 to the de-matching layer 104. The de-matching layer 104 then provides the connection to the flex circuit, application specific integrated circuit (ASIC), or other interconnect structure.

Figure 3:
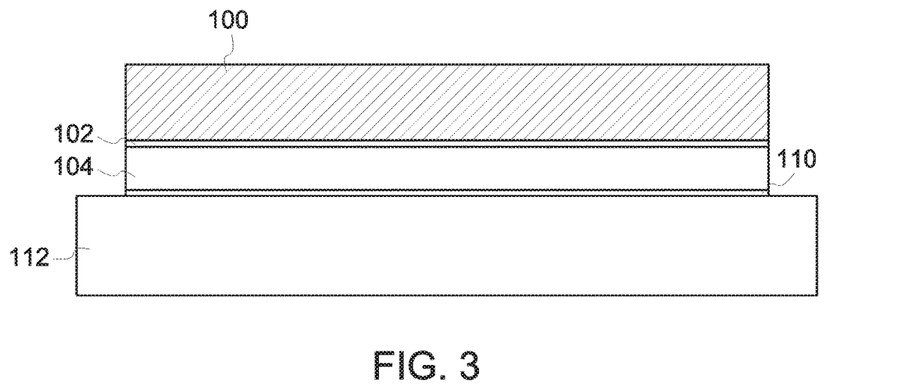
FIG. 3 depicts the piezoelectric transducer layer and a de-matching layer of FIG. 2 bound to a carrier, in accordance with aspects of the disclosure.

Turning to FIG. 3, the de-matching layer 104 and piezoelectric transducer layer 100 (with the electrode 102 between the two) are positioned on a removable, rigid carrier 112. The carrier 112, once bound to the de-matching layer 104 and piezoelectric transducer layer 100, allows these layers to be diced and prepared, as discussed in greater detail below.

This stack assembly may be laminated and may be bonded to the carrier 112 using a releasable adhesive 110 (e.g., an ultraviolet (UV) releasable adhesive on a quartz carrier, a blue-light releasable adhesive on a glass carrier, or a chemically releasable adhesive). Alternatively, the piezoelectric transducer layer 100 and de-matching layer may be bonded to a thermally-conductive carrier 112 using a thermally releasable adhesive. In yet another implementation, instead of a releasable adhesive 110 and carrier 112, the carrier 112 may instead be easy to grind away so that, in a subsequent step, the carrier 112 may be ground away instead of released.

Figure 4:
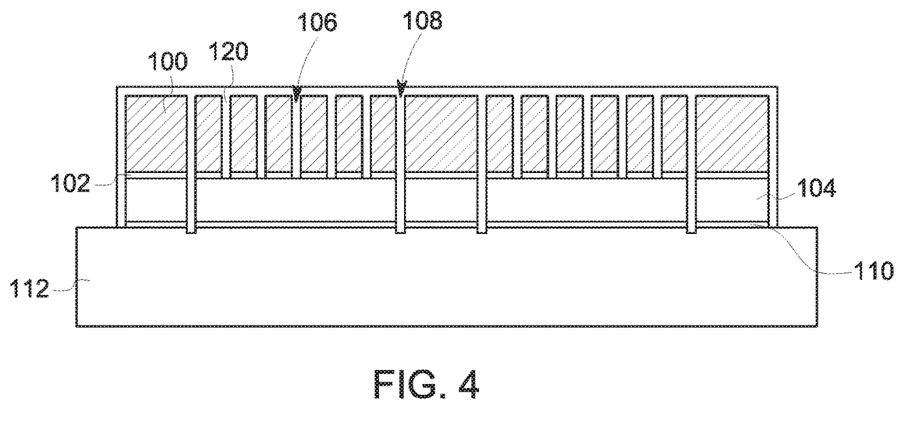
FIG. 4 depicts an elevation view of the stack of FIG. 3 after initial dice and fill operations, in accordance with aspects of the disclosure.

Turning to FIG. 4, an elevation-view of the laminated acoustic stack is shown. In one implementation, as shown in FIG. 4, the stack undergoes two dicing operations, a composite cut operation through the piezoelectric transducer layer 100 (composite cuts 106) and a deeper isolation cut operation through both the piezoelectric transducer layer 100 and de-matching layer 104 (isolation cuts 108). The composite cut operation is optional and, when present, the composite cuts 106 are made to facilitate fabrication of a composite piezoelectric transducer layer, as discussed below.

As shown, the isolation cuts 108 are filled with a first material 120 (e.g., a first epoxy) and allow the formation of wrap-around grounds. The isolation cuts 108 serve to isolate the transducer elements from the ground path.

Conversely, the composite cuts 106 are made within respective transducer arrays and are employed when the piezoelectric transducer layer 100 is fabricated as a piezoelectric composite layer. In the depicted example, the composite cuts 106 pass through the piezoelectric transducer layer 100, but not the de-matching layer 104 and are filled with the material 120 or other suitable materials. Piezocomposite materials which may be formed from the composite cuts 106 typically combine piezoelectric elements (e.g., the piezo material forming the layer 100) with a passive polymer, such as an epoxy, or an active polymer (filler material 120). The piezo-composite, when present as the piezoelectric transducer layer 100, may be characterized according to its connectivity (e.g., 1-3, 2-2, 0-3, and so forth), where the first number in the sequence refers to the number of dimensions through which the piezoelectric material is continuous and the second number refers to the number of dimensions through which the filler material 120 is continuous.

The use of composite piezoelectric transducers, when present, allow the use of lower-impedance matching layers than are required with a solid piezoelectric transducer. Such lower-impedance matching layers are easier to manufacture, especially via additive processes, as discussed herein. Further, the use of composite piezoelectric transducers on the de-matching layer 104 as shown in the present examples is believed to provide acoustic and electrical performance similar to solid piezoelectric transducers without a de-matching layer 104, and should allow use of lower-impedance, undiced matching layers (discussed below), eliminating process steps and reducing cost.

Figure 5:
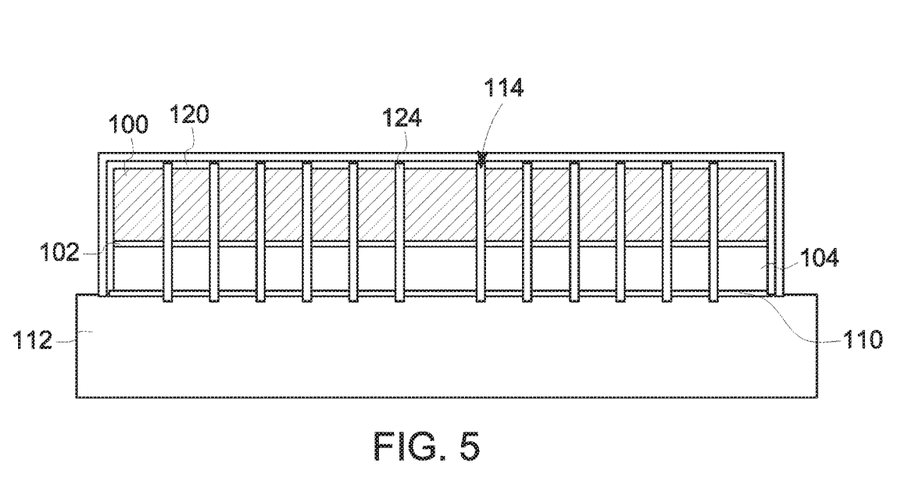
FIG. 5 depicts an azimuth view of the stack of FIG. 4 after further dice and fill operations, in accordance with aspects of the disclosure.

Turning to FIG. 5, the view is rotated 90 degrees to depict an azimuthal view of the acoustic stack. At the step shown in FIG. 5, another dice operation is performed to form element cuts 114 (perpendicular to the isolation cuts) through both the piezoelectric transducer layer 100 and de-matching layer 104. The element cuts 114 are filled with either the first epoxy 102 or, as shown, a second material (e.g., a second epoxy) 124 different from the first material. In particular, in certain implementations a second epoxy 124 is employed to fill the element cuts 114 so as to minimize or reduce cross-coupling between the formed elements. If undiced acoustic matching layers introduce an undesired degree of crosstalk, element dicing may be deferred to a later step after one or both matching layers are added so as to also element dice the matching layers as well.

In certain implementations a sub-dice step may also be performed. As used herein, sub-dicing involves connecting two or more mechanical elements to create one electrical element and may help to control resonance modes of vibration. By way of example, in one implementation, a sub-dice step may be performed through the piezoelectric transducer layer 100 only so as to help control resonance modes. Sub-dicing, if performed, should occur before the matching layers are added.

Figure 6:
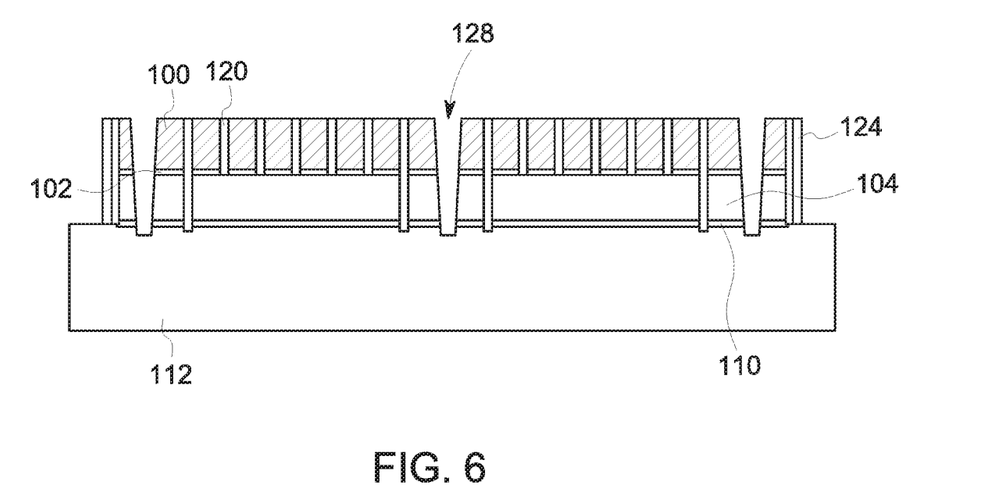
FIG. 6 depicts an elevation view of the stack of FIG. 5 after an additional dice operation, in accordance with aspects of the disclosure.

Turning to FIG. 6, an elevation view of the acoustic stack is once again shown. In this depicted step, the piezoelectric transducer layer 100 is ground to its desired thickness, removing any overlying coating of the first material (e.g., first epoxy) 120 and/or second material (e.g., second epoxy) 124. In the depicted step, a number of dicing cuts 128 (e.g., wide, deep cuts) are made through the piezoelectric transducer layer 100 and de-matching layer 104. The cuts 128 may be tapered and expose edges of the formed arrays to allow wrap-around ground connections to be formed.

Figure 7:
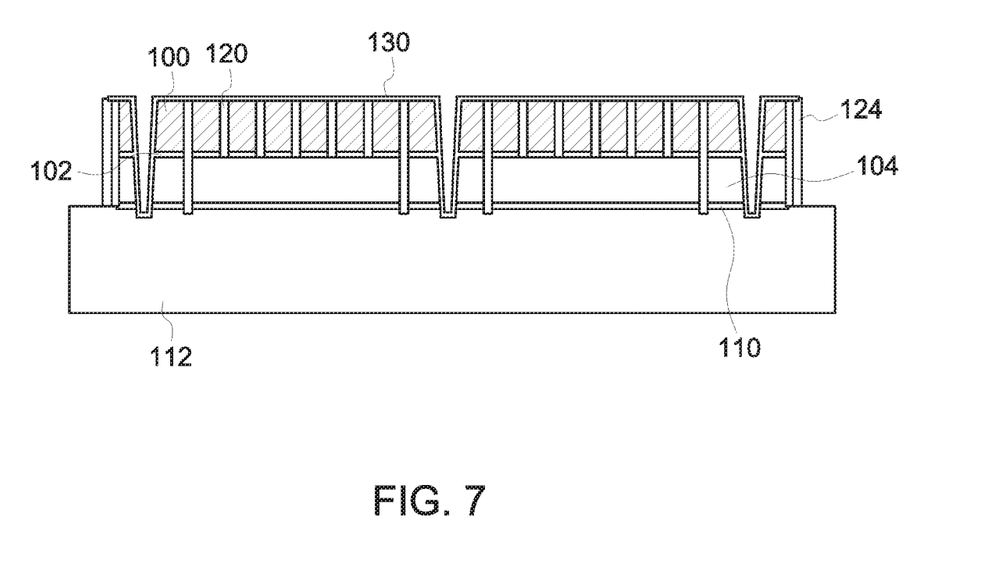
FIG. 7 depicts an elevation view of the stack of FIG. 6 after formation of a wrap-around electrode, in accordance with aspects of the disclosure.

Turning to FIG. 7, the formation of the wrap-around ground connections is shown. The wrap-around ground electrode 130 is formed using one or more standard metallization techniques (such as sputtering, plating) and/or additive manufacturing/3D printing processes (such as controlled dispensing, jetting, and so forth) and curing of a highly conductive ink (e.g., nanoparticle- or organometallic-based silver, copper, or gold). In particular, the ground electrode 130 is formed on top of the piezoelectric transducer layer 100 and wraps-around the diced edges of the piezoelectric transducer layer 100 and de-matching layer 104. The wrap-around ground electrode forms an electrical connection between the signal and ground sides of the piezoelectric transducer layer 100 without blocking or interfering with the acoustic path.

Figure 8:
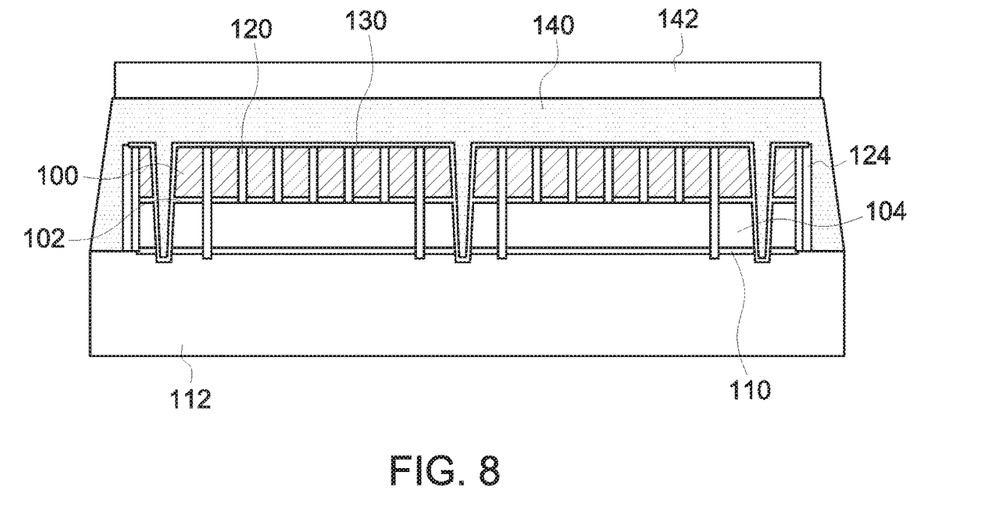
FIG. 8 depicts an elevation view of the stack of FIG. 7 after addition of matching layers, in accordance with aspects of the disclosure.

Turning to FIG. 8, and maintaining the elevation view perspective, one or more acoustic matching layers 140, 142 are added to the acoustic stack. In the depicted example, two acoustic matching layers 140, 142 are added. In one implementation, one or more of the acoustic matching layers 140, 142 are printed (i.e., added by additive manufacturing techniques, such as 3D printing) onto the acoustic stack. As part of the printing process, one or both matching layers 140, 142 may be patterned, such as including "cuts" (i.e., voids or empty regions) to reduce inter-element crosstalk. As noted above, in certain implementations the element dicing (and kerf filling) may be performed after one or both of the acoustic matching layers 140, 142 are added at this step, thus forming the element cuts 114 in one or both of the acoustic matching layers 140, 142.

As discussed herein, if a composite piezoelectric material is fabricated as part of the piezoelectric transducer layer 100, the composite piezoelectric material may allow the use of lower-impedance acoustic matching layers than might otherwise be used, e.g., lower impedance that those used with solid piezoelectric transducers. Such lower-impedance acoustic matching layers 140, 142 are easier to manufacture, particularly via additive processes as discussed herein, and may use materials having lower shear stiffness, and thus lower inter-element coupling (crosstalk) if the acoustic matching layers are not diced at a transducer element level. Low-cost transducers with undiced matching layers should therefore be easier to make and have better performance (e.g., less crosstalk) if made with composite piezoelectric transducers as discussed herein.

Figure 9:
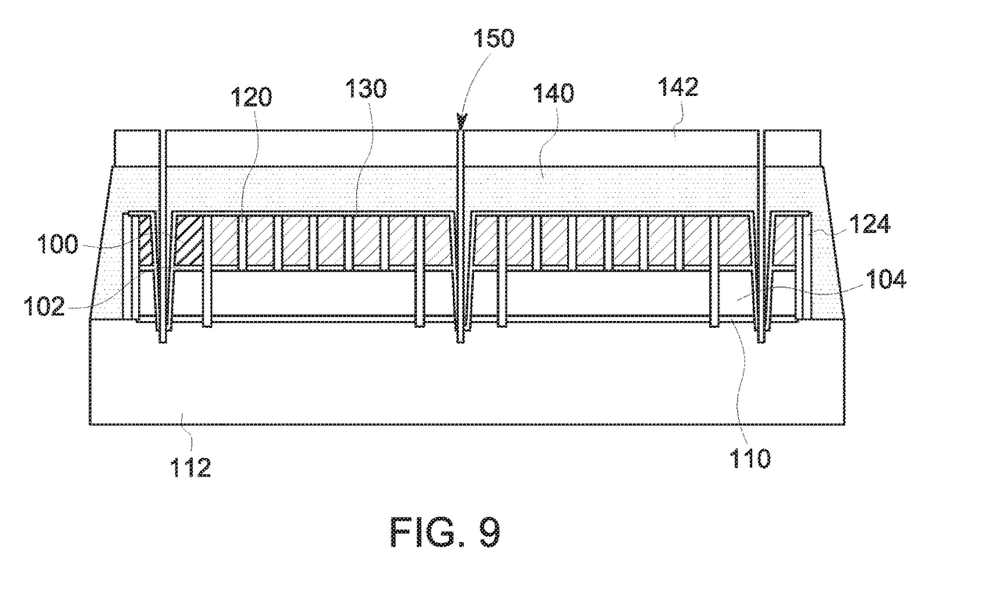
FIG. 9 depicts an elevation view of the stack of FIG. 8 after a final dice operation, in accordance with aspects of the disclosure.

Turning to FIG. 9, and maintaining the elevation view perspective, dice cuts 150 are made in the assembled acoustic stack through the matching layers 140, 142 where the matching layer material is present in the previously formed dicing cuts 128. The areas delineated by the dice cuts 150 correspond to the transducer arrays being fabricated.

Figure 10:
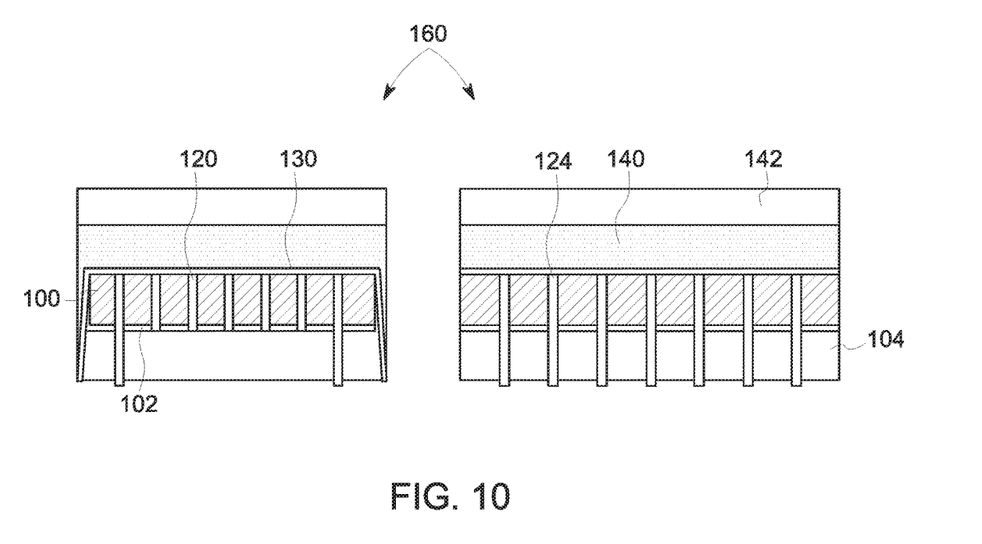
FIG. 10 depicts elevation and azimuth views of a transducer array after release from the carrier, in accordance with aspects of the disclosure.
Figure 11:
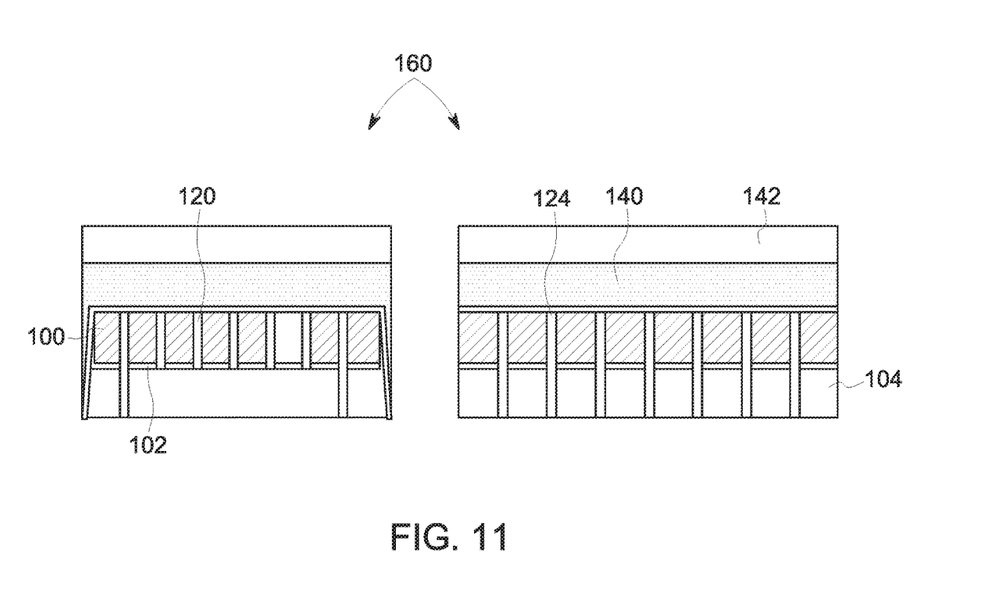
FIG. 11 depicts elevation and azimuth views of the transducer array of FIG. 10 after a grinding operation, in accordance with aspects of the disclosure.
Figure 12:
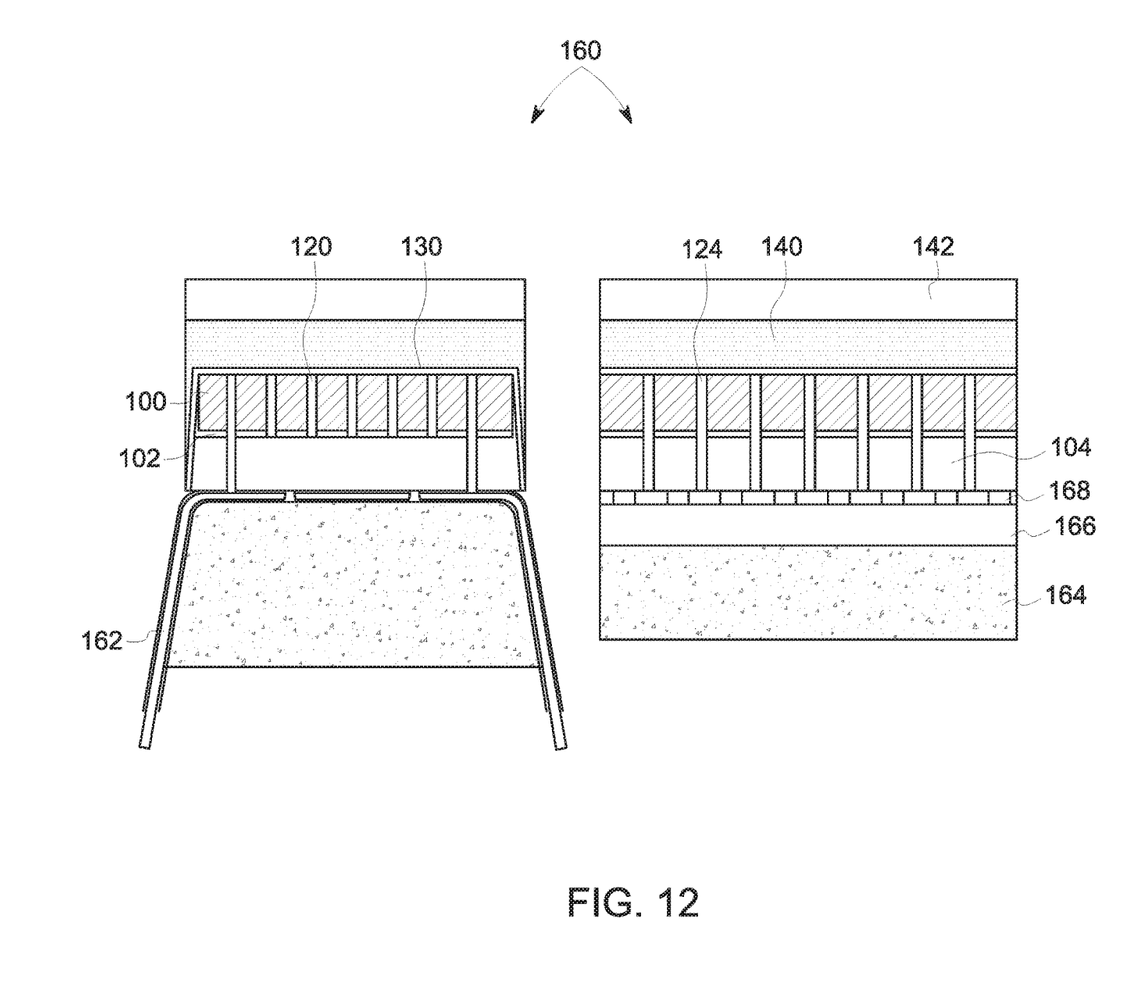
FIG. 12 depicts elevation and azimuth views of the transducer array of FIG. 11 after attachment to an ASIC or flex circuit, in accordance with aspects of the disclosure.

FIGS. 10-12 for completeness, shown both elevation views (leftmost) and azimuth views (rightmost) of the respective steps. As these steps occur after dice cuts 150 have separated the individual transducer arrays, the respective views also depict, from the elevation and azimuth perspectives, a single array 160 as opposed to the bulk-manufacture array stack. Turning to FIG. 10, at this step, each array 160 is released from the carrier 112, either by exposing the releasable adhesive 110 to the environmental condition (e.g., heat, blue light, UV, chemical agent) that causes the adhesive 110 to release or by grinding the carrier 112 away.

Turning to FIG. 11, once the carrier 112 is removed, the exposed surface (i.e., the bottom) of the de-matching layer 104 may be cleaned and/or flattened, such as by grinding or other suitable processing, for subsequent electrical connection to the imaging system circuitry, such as a probe component. In one implementation, the de-matching layer 104 is fabricated using a hard material, which allows cleaning of the de-matching layer after its release by grinding or other mechanical approaches without changing the thickness of the acoustic layer (i.e., piezoelectric transducer layer 100 and matching layers 140, 142).

In one implementation, electrical and/or acoustic testing of the arrays 160 is performed using the exposed conductive contacts of the arrays 160. In this manner, faulty arrays 160 may be discarded before further processing, i.e., prior to attachment to the driving and readout circuitry.

Turning to FIG. 12, successfully tested arrays 160 are connected to the circuitry to be used in manufacturing a probe assembly. For example, arrays 160 may be picked and placed such that the array 160 is electrically connected to a flex circuit 162 on an acoustic backing 164 (shown on the left) or may be connected via conductive bumps 168 to an ASIC 166 provided on the backing 164 (shown on the right). In certain implementations, signals traces may be fabricated using additive manufacturing/printing processes (such as controlled dispensing, jetting, and so forth) and curing of a highly conductive ink (e.g., nanoparticle- or organometallic-based silver, copper, or gold) on the backing 164 and/or may be laser-structured on the backing 164.

Technical effects of the invention include the bulk manufacture of transducer arrays having at least one 3D printed (or otherwise additive manufactured) acoustic matching layers. In certain implementations, the manufactured transducers are composite-piezoelectric transducers on de-matching layers and have performance equivalent to or superior to transducers fabricated with the same or similar materials and dimensions using traditional (lamination) processes. Performance of composite-piezoelectric transducers on de-matching layers, using the disclosed process, should be similar to performance of traditional solid-piezoelectric transducer transducers without de-matching layer. In one implementation, by producing multiple arrays at once on a common carrier, and by using direct-deposit additive processes for the matching layers, the described process greatly reduces the number of parts and the number of manual operations. This process should be capable of partial or full automation, which should dramatically increase production capacity and reduce product cost.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for fabricating ultrasound transducers, comprising:
   providing a piezoelectric transducer layer at an initial thickness;
   forming a signal electrode on one surface of the piezoelectric transducer layer to form a signal surface of the piezoelectric transducer layer;
   positioning a de-matching layer against the signal electrode opposite the piezoelectric transducer layer;
   positioning the de-matching layer and the piezoelectric transducer layer on a carrier;

forming a plurality of isolation cuts through both the piezoelectric transducer layer and the de-matching layer, wherein the isolation cuts isolate the transducer elements from a ground path;

forming a plurality of composite cuts through the piezoelectric transducer layer but not the de-matching layer;

filling the isolation cuts and the composite cuts with a first material;

forming a plurality of element cuts through both the piezoelectric transducer layer and the de-matching layer, wherein the element cuts run perpendicular to the isolation cuts and define transducer elements within each transducer array;

filling the element cuts with the first material or a second material;

grinding the piezoelectric transducer layer to a specified thickness to form a ground surface of the piezoelectric transducer layer;

forming a plurality of initial dicing cuts through both the piezoelectric transducer layer and the de-matching layer, wherein the initial dicing cuts define two or more transducer arrays;

forming a wrap-around ground electrode over the diced piezoelectric transducer layer and the de-matching layer, wherein the wrap-around ground electrode connects the signal surface and the ground surface of the piezoelectric transducer layer without blocking an acoustic path of the respective transducer arrays;

forming one or more acoustic matching layers over the piezoelectric transducer layer opposite the de-matching layer using additive manufacturing processes and wherein the one or more acoustic matching layers includes a plurality of additional cuts or voids through the one or more acoustic matching layers and corresponding to the initial dicing cuts; and releasing a stack assembly comprising at least the one or more acoustic matching layers, the piezoelectric transducer layer, and the de-matching layer from the carrier, wherein the plurality of transducer arrays corresponding to stack assembly regions defined by the dicing cuts is released.

2. The method of claim 1, wherein the piezoelectric transducer layer in combination with the composite cuts and the first material comprise a composite piezoelectric layer.

3. The method of claim 2, wherein the composite piezoelectric layer has one of a 1-3 composite configuration and a 2-2 composite configuration.

4. The method of claim 1, wherein a releasable adhesive is used to adhere the de-matching layer to the carrier.

5. The method of claim 1, where one or both of the first material and the second material comprise a polymeric composition or an epoxy.

6. The method of claim 1, wherein the additive manufacturing processes used to form the at least one or more acoustic matching layers comprise a 3D printing process.

7. The method of claim 1, wherein the at least one or more acoustic matching layers are patterned.

8. The method of claim 1, wherein releasing the stack assembly comprises exposing the carrier to an environmental condition that releases a releasable adhesive binding the carrier to the de-matching layer.

9. The method of claim 8, wherein the environmental condition comprises one of ultraviolet radiation, blue light, heat, and a chemical aunt.

10. The method of claim 1, further comprising connecting contacts present on the de-matching layer of each said transducer array to respective circuitry used to drive and readout the respective transducer array.

11. The method of claim 10, further comprising cleaning or grinding a surface of the de-matching layer released from the carrier prior to connecting each said transducer array to the respective circuitry.

12. A method for fabricating ultrasound transducers, comprising:

providing a piezoelectric transducer layer at an initial thickness;

forming an electrode on one surface of the piezoelectric transducer layer to form a signal surface of the piezoelectric transducer layer;

positioning a de-matching layer against the signal surface opposite the piezoelectric transducer layer;

positioning the de-matching layer and the piezoelectric transducer layer on a carrier;

forming a plurality of isolation cuts through both the piezoelectric transducer layer and the de-matching layer, wherein the isolation cuts isolate the transducer elements from a ground path;

filling the isolation cuts with a first material;

forming a plurality of element cuts through both the piezoelectric transducer layer and the de-matching layer, wherein the element cuts run perpendicular to the isolation cuts and define transducer elements within each transducer array;

filling the element cuts with the first material or a second material;

grinding the piezoelectric transducer layer to a specified thickness to form a ground surface of the piezoelectric transducer layer;

forming a plurality of initial dicing cuts through both the piezoelectric transducer layer and the de-matching layer, wherein the initial dicing cuts define two or more transducer arrays;

forming a wrap-around ground electrode over the diced piezoelectric transducer layer and the de-matching layer, wherein the wrap-around around electrode connects the signal surface and the ground surface of the piezoelectric transducer layer without blocking an acoustic path of the respective transducer arrays;

forming one or more acoustic matching layers over the piezoelectric transducer layer opposite the de-matching layer using additive manufacturing processes and wherein the one or more acoustic matching layers includes a plurality of additional cuts or voids through the one or more acoustic matching layers and corresponding to the initial dicing cuts; and releasing a stack assembly comprising at least the one or more acoustic matching layers, the piezoelectric transducer layer, and the de-matching layer from the carrier, wherein the plurality of transducer arrays corresponding to stack assembly regions defined by the dicing cuts is released.

13. The method of claim 12, wherein the additive manufacturing processes used to form at least one or more acoustic matching layers comprise a 3D printing process.

14. The method of claim 12, wherein the at least one or more acoustic matching layers are patterned.

15. The method of claim 12, wherein releasing the stack assembly comprises exposing the carrier to an environmental condition that releases a releasable adhesive binding the carrier to the de-matching layer.

16. The method of claim 12, further comprising connecting contacts present on the de-matching layer of each said transducer array to respective circuitry used to drive and readout the respective transducer array.

* * * * *